United States Patent
Ruddle

Patent Number: 5,879,160
Date of Patent: Mar. 9, 1999

[54] ROOT CANAL OBSTRUCTION REMOVAL SYSTEM

[76] Inventor: Clifford J. Ruddle, 227 Las Alturas Rd., Santa Barbara, Calif. 93103

[21] Appl. No.: 89,768
[22] Filed: Jun. 3, 1998
[51] Int. Cl.[6] .................................................... A61C 3/00
[52] U.S. Cl. ........................................ 433/141; 433/102
[58] Field of Search .................................. 433/102, 141, 433/224, 153, 163

[56] References Cited

U.S. PATENT DOCUMENTS

| | | | |
|---|---|---|---|
| 3,322,124 | 5/1967 | Ireland | 433/141 |
| 4,247,285 | 1/1981 | Roig-Greene | 433/141 |
| 4,746,292 | 5/1988 | Johnson | 433/141 |
| 4,904,185 | 2/1990 | McSpadden | 433/164 |
| 5,173,049 | 12/1992 | Levy | 433/215 |
| 5,658,149 | 8/1997 | Munce | 433/102 |

*Primary Examiner*—John J. Wilson
*Assistant Examiner*—Patrick A. Hilsmier
*Attorney, Agent, or Firm*—Polster, Lieder, Woodruff & Lucchesi

[57] ABSTRACT

Briefly stated, the present invention provides a kit which facilitates the removal of obstructions, such as broken files, from the root canal of a patient during an endodontic or root canal procedure. The kit includes a trephine sized to be inserted in the root canal and adapted to widen the root canal around the obstruction to expose the obstruction and an obstruction removal tool adapted to engage and mechanically grasp the obstruction to remove the obstruction from the root canal. The obstruction removal tool includes a hollow tube and a plunger slideable within the tube. The hollow tube is sized to be inserted into the root canal a distance sufficient to receive the obstruction within its lumen. A cutout is spaced from the end of the hollow tube, and the hollow tube is slid over the obstruction a distance sufficient to generally align the top of the obstruction with the cutout. A plunger having a beveled end is slid through the hollow tube. The beveled end of the plunger engages the obstruction and urges the obstruction into the cutout so that the tool will mechanically grasp the obstruction. Once the tool has mechanically grasped the obstruction, the tool with the obstruction can be removed from the root canal.

15 Claims, 3 Drawing Sheets

ROOT CANAL OBSTRUCTION REMOVAL SYSTEM

BACKGROUND OF THE INVENTION

This invention relates to a method for retrieving obstructions, such as broken instruments, from the root canals of human teeth, during endodontic and retreatment procedures. Specifically, the invention relates to a set of microendodontic instruments precisely designed and machined to remove a broken instrument from deep within the root canal space.

The human tooth contains a clinical crown and root. The crown portion has a thin outer layer of enamel which covers the underlying tubular dentine. The root's outer layer is comprised of a thin layer of cementum which covers the radicular dentine. Harbored deep and generally running central within these hard tissue structures is the soft tissue called the dental pulp which provides the vascular support and neural supply for the human tooth.

Throughout life, the dental pulp is vulnerable to injuries from decay (microbial), trauma (physical injuries), extensive dental procedures, or in certain instances, periodontal disease. These injuries singularly, or in combination, predispose the dental pulp to a cascade of pathological conditions beginning with inflammation and concluding with necrosis.

When these events transpire, patients may present in a dental office with clinical symptoms which, often times, demonstrate abnormalities of the soft tissue, supporting structures, and/or exhibit radiographic evidence of bone loss. The treatment options include palliative emergency care, endodontics (i.e., root canal treatment), or extraction. In other instances patients present with signs and/or symptoms associated with a failing endodonitically treated tooth that requires retreatment or extraction.

To avoid extraction of the tooth, root canal treatment or retreatment is performed. The root canal treatment is directed towards the elimination of pulp, bacteria, and irritants from the root canal system, followed by filling the canal space with an inert, biocompatible, dimensionally stable, root canal filling material. The clinical chain of treatment events are typically anesthesia and isolation procedures followed by cleaning and shaping procedures ideally culminating in three-dimensional obturation of the complex root canal space.

Canal preparation is accomplished utilizing instruments commonly referred to as "files". Manufacturers provide the doctor with a great variety of file choices ranging from different metals to flute configurations and geometries, tapers, lengths, and handle designs. Additionally, files can be used by hand or rotary instrumentation techniques. During cleaning and shaping procedures, the potential for file breakage is always present. File breakage is further impacted by the quality of manufacturing of the instrument used, the metallurgical properties of the metal from which the instrument is made, the number of times an instrument has previously been used, the degree of calcification, curvature, and length of a particular root canal system, patient cooperation, and importantly, method of use.

Historically retrieving broken instruments or other intercanal obstructions, such as gates glidden drills, lentulo spirals, silver points, and obturation carriers, posed formidable challenges. A broken instrument clearly compromises the prognosis of a case. The instrument can break at any point in the canal. If the coronal end of the broken instrument is near the crown of the tooth, the instrument can be removed fairly easily using traditional or conventional techniques. However, if the instrument breaks deep within the root canal, for example, where the canal begins to bend or curve, extraction of the instrument becomes much more difficult. Currently available retrieval instruments used to retrieve broken instruments cannot reach deep into the root canal, and thus cannot be used when the broken instrument is deep within the root canal. Because the practitioner was still in the process of cleaning and shaping the root canal, there can be bacteria, pulp, endotoxins, etc. deeper in the root canal that still needs to be removed. Thus, breakage of the instrument deep within the root canal can severely impact the outcome of the endodontic procedure.

Typically, the patient is faced with two options when the instrument breaks deep within the root canal. One option is extraction of the tooth. The other option is apical surgery to seal off the end of the root to prevent the bacteria, pulp, edotoxins, etc. from leaking out the end of the root canal.

Over time various retrieval techniques evolved that were crude, often times ineffective, and limited by restricted space. Frequently, efforts directed towards instrument retrieval, even when successful, weakened roots due to overzealous canal enlargement, which in turn predisposed the tooth to subsequent root fractures and, ultimately, the loss of a tooth. Additionally, attempting to remove a broken instrument can lead to serious iatrogenic events, such as perforation of the root or the creation of ledges within the root canal, which can alter prognosis. If retrieval efforts are unsuccessful, cleaning and shaping procedures and obturation are compromised and the ultimate prognosis in placed in doubt.

Lighting and magnification equals vision and are critically essential for safe and successful instrument removal. The introduction of the dental operating microscope has certainly allowed clinicians good looks at the problems. Traditionally, small files were used in efforts to either bypass or eliminate the broken instrument. Varying diameter tubes have been advocated and are placed over the most coronal end of the obstruction and are utilized in a variety of ways to retrieve obstructions. Tubes are attached to the obstruction by glue, mechanical friction, or internal threads which engage certain broken instruments. The most recent advancement in broken instrument removal utilizes ultrasonic systems. Specific ultrasonic instruments have evolved and play a central role in removing broken instruments. Even with all the innovations directed towards safe and successful instrument retrieval a small but statistically significant number of broken instruments can not be retrieved with existing technologies and techniques. Therefore, the present invention provides a device that facilitates the removal of broken instruments and other intercanal obstructions from root canal systems.

BRIEF SUMMARY OF THE INVENTION

Briefly stated, the present invention provides a kit which facilitates the removal of obstructions, such as broken files, from the root canal of a patient during an endodontic or retreatment procedure. The kit includes a trephine and a tool adapted to grasp and remove the obstruction. The trephine is sized to be inserted in the root canal and is adapted to widen the root canal around the obstruction to expose the obstruction. The obstruction removal tool engages and mechanically grasps the obstruction to remove the obstruction from the root canal. The trephine is a slightly flexible tube having a hollow bottom end with a cutting edge. The cutting edge of the bottom end is preferably made of cutting flutes. The hollow bottom end has an inner diameter slightly larger then an upper end of the obstruction so that the trephine will cut around the obstruction to widen the root canal in the vicinity of the obstruction.

The obstruction removal tool includes a hollow tube and a plunger or wedge slideable within the tube. The hollow tube is also slightly flexible and defines a lumen. The tube has a bottom end, a top end and a cutout spaced from the bottom end. The hollow tube has an outer diameter sized to be received in the root canal and an internal diameter sized to admit the obstruction into the lumen. A retainers or hold extends outwardly from an outer surface of the tube to facilitate removal of the tube from the root canal once the obstruction has been grasped by the tool.

The plunger is sized to be slidably received in the hollow tube from the top end of the tube. The plunger has a length sufficient to extend at least to the cutout in the hollow tube and has a bottom end and a top end. The bottom end of the plunger is beveled to push a top end of the obstruction into the cutout. The plunger and tube cooperate to mechanically grasp the obstruction.

The tool includes a guide which properly orients the bottom of the plunger in the hollow tube, such that said beveled end of said plunger faces said cutout of said hollow tube. The guide includes a rib on the plunger and a groove or slot on the tube which are positioned on the respective parts to properly orient the beveled end of the plunger when the plunger engages the obstruction.

In operation, the trephine is used to widen the root canal around the top of the obstruction. The tube is then slid into the root canal until the obstruction is received in the end of the tube and the top of the obstruction is generally aligned with the cutout in the tube. The plunger is then inserted into the tube until it engages the obstruction. The guides on the tube and plunger orient the beveled end of the plunger so that it faces the cutout. The plunger is then pushed a bit further into the tube to urge the top of the obstruction into the cutout. In this position, the plunger and the tube cooperate to mechanically grasp or hold the obstruction. The tool, which is holding the obstruction, can then be removed from the root canal to remove the obstruction from the root canal.

BRIEF DESCRIPTION OF THE SEVERAL VIEWS OF THE DRAWINGS

Corresponding reference numerals will be used throughout the several figures of the drawings.

DETAILED DESCRIPTION OF THE INVENTION

The following detailed description illustrates the invention by way of example and not by way of limitation. This description will clearly enable one skilled in the art to make and use the invention, and describes what I presently believe is the best mode of carrying out the invention.

Figure 1:
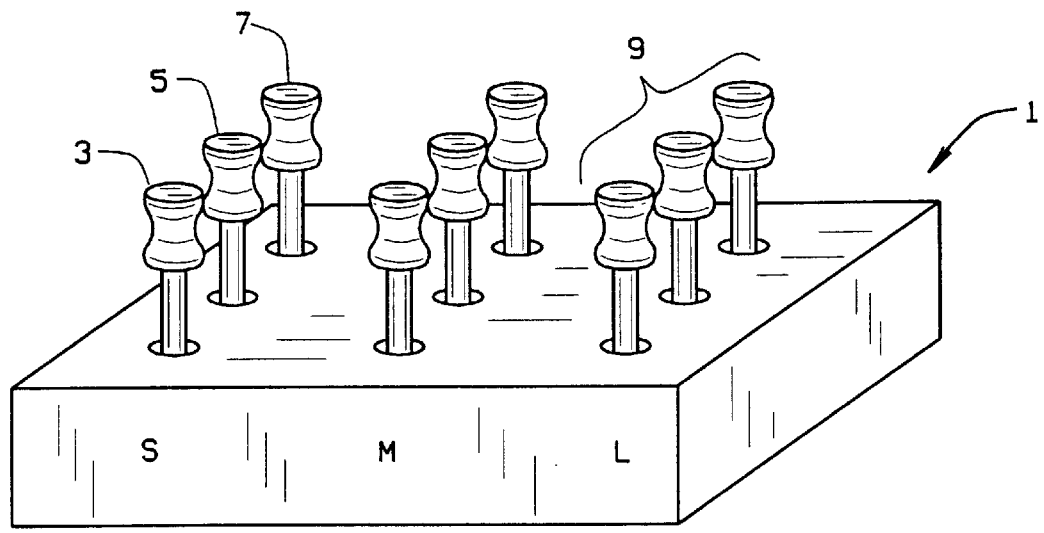
FIG. 1 is a perspective view of an obstruction removal kit of the present invention.

An instrument removal kit 1 of the present invention comprises sets of three instruments (a microtrephine 3, a microtube 5, and an insert wedge or plunger 7) which are used in conjunction with each other to remove an obstruction O, such as a piece of broken file, from the root canal RC of a tooth T. The instruments 3, 5, and 7 comprise a set 9 of instruments designed to remove obstructions O of varying sizes from the root canal RC. There are three sets 9 shown in FIG. 1. The three instruments of each set are sized to work together. Thus each set 9 is of a different size (i.e., small, medium, and large) to enable the practitioner to remove obstructions of different sizes.

Figure 4:
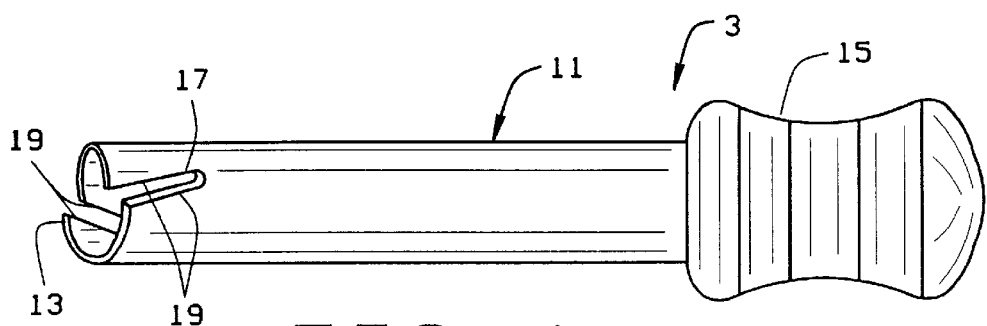
FIG. 4 is a side elevational view of a trephine used to enlarge the root canal to expose the top or coronal portion of the obstruction.

The microtrephine 3 (FIG. 4) comprises a hollow tube 11 having an open front end 13 and a handle 15 at its back end. The microtrephine has specific inner diameter and an outer diameter. The front end 13 of the microtrephine tube 11 has a pair of oppositely positioned grooves 17 to define cutting flutes 19.

Figures 2, 3:
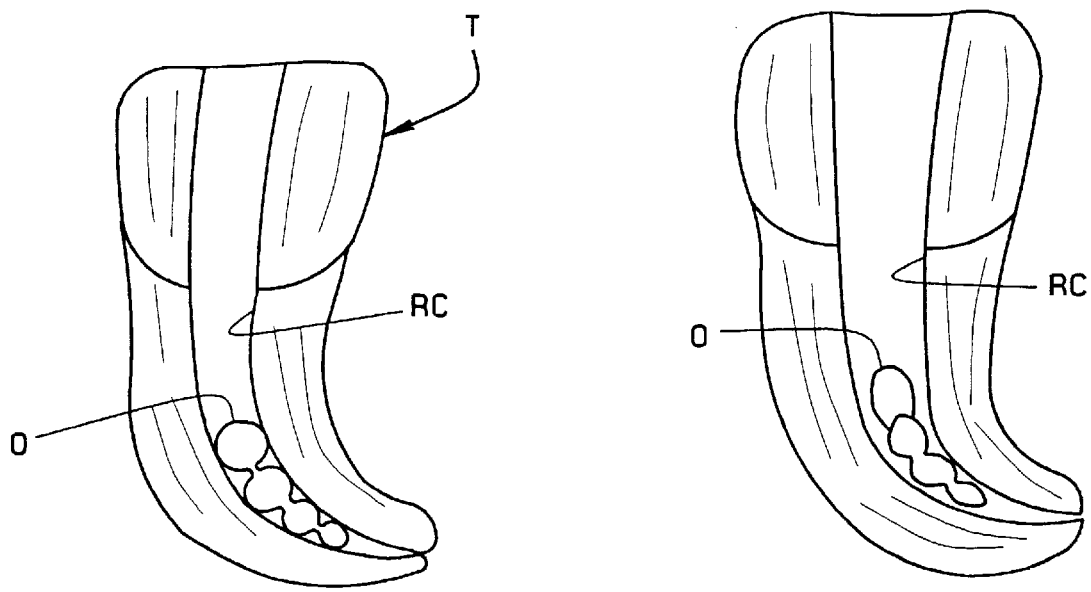
FIG. 2 is a cross-sectional view of a tooth having an obstructed root canal.
FIG. 3 is a cross-sectional view of the tooth, with the canal enlarged to expose the top of the obstruction for removal of the obstruction.

The microtrephine 3 is sized to be received in the root canal RC. It is used to form a radicular access to expose and subsequently visualize the coronal most end of the broken instrument or obstruction O. As shown in FIG. 2, the obstruction is substantially as wide as the root canal RC. The microtrephine is used to widen the access to the root canal RC as shown in FIG. 3. The microtrephine is then used to circumferentially expose 2–3 mm of the most coronal aspect of the instrument. (FIG. 3). This procedure is accomplished by selecting and using a properly sized microtrephine 3. The inside diameter of the selected microtrephine 3 corresponds to the diameter of the broken instrument or obstruction O. The handle 15, and hence the microtrephine 3, is rotated clockwise allowing its distal flutes 19 to precisely cut dentine circumferentially around the obstruction O. The trephine 3 is slightly flexible. Thus, the broken instrument or obstruction O itself serves as a guide. Stated differently, as the trephine is used to widen the root canal around the broken instrument, the instrument (which is already flexed to the general curvature of the root) will guide the trephine, and the trephine will flex or bend to the curvature of the instrument as the trephine widens the root canal. This substantially prevents the creation of a false pathway and hence, reduces the possibility of perforating the root canal or causing other iatrogenic events. This cutting action is continued, as noted, until about 2–3 mm of the instrument head is exposed. (FIG. 3). When the obstruction is properly exposed for removal or extraction, the microtrephine is removed from the root canal.

Figure 5:
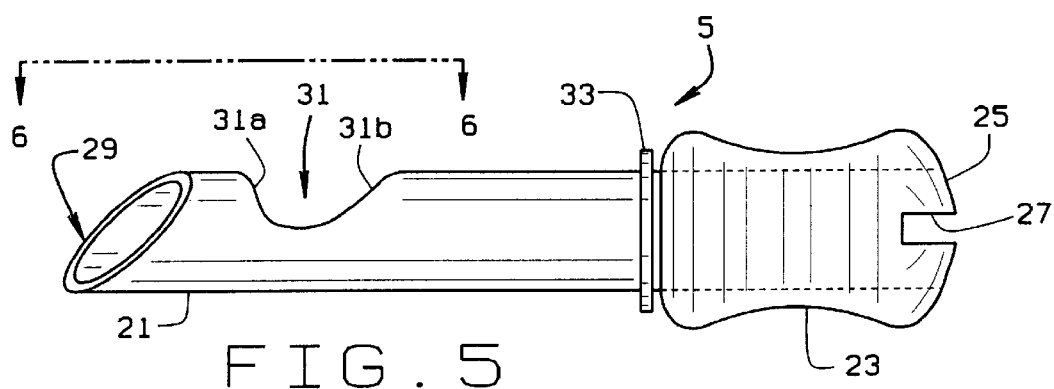
FIG. 5 is a side elevational view of a microtube used to remove the obstruction from the root canal.
Figure 6:
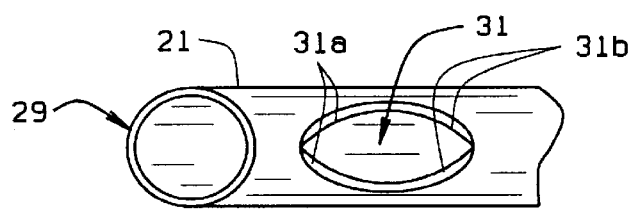
FIG. 6 is a side elevational view of the microtube offset 90° from FIG. 5, and taken along line 6—6 of FIG. 5.
Figure 7:
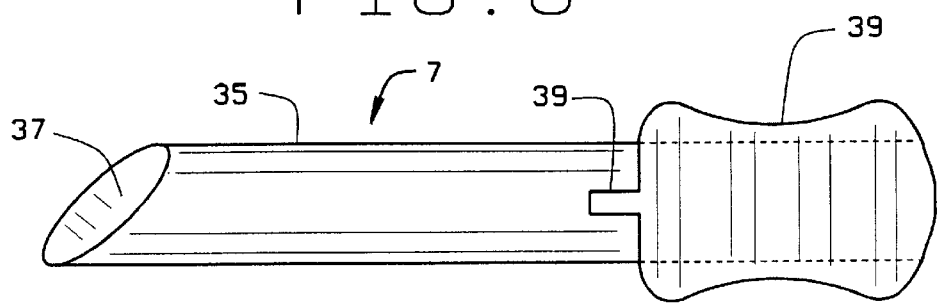
FIG. 7 is a side elevational view of an insert wedge or plunger used in conjunction with the microtube to remove the obstruction.

Next, a microtube 5 is inserted in the root canal RC to surround the exposed end of the obstruction O. The microtube 5 (FIGS. 5 and 6) has a tubular body 21 with a handle 23 at its top or back end 25. The tube is hollow, and defines a lumen which extends the length of the tube and is open at both its top and bottom ends. A pair of slots 27 extend downwardly from the top end 25 of the microtube 5. The front end 29 of the microtube 5 is opened. Preferably, the front end 29 is beveled, preferably at 45°. A cutout 31 is formed in the tube 5 slightly above the front end 29. The cutout 31 has a fairly flat bottom edge 31a (that is, the bottom edge forms an angle of about 80° to about 100° with the longitudinal axis of the tube 5) and a sloped top edge 31b. A hold 33 extends radially from the microtube 5 below the handle 23 and above the cutout 31. The hold 33 preferably extends circumferentially around the tube 5.

Figure 8:
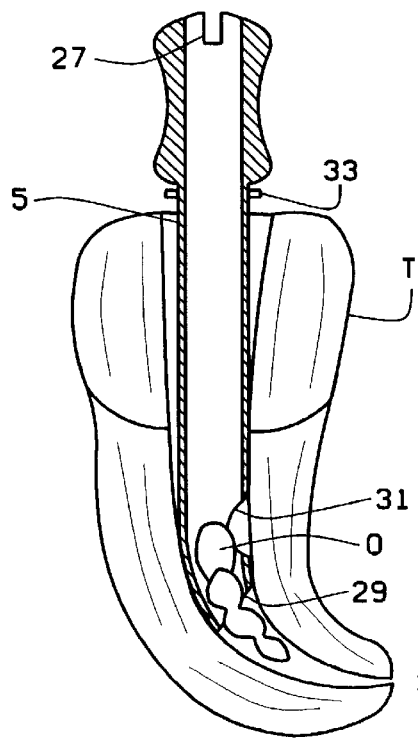
FIG. 8 is a side elevational view of the microtube placed over the obstruction for removal of the obstruction.

The microtube's inner and outer diameters correspond to the inner and outer diameters of the microtrephine which was used to expose the obstruction O. The microtube is inserted into the enlarged root canal RC and placed over the previously exposed instrument O, as seen in FIG. 8. If applicable, the beveled end 29 of the microtube 5 pushes the broken instrument's head off a canal wall and into its lumen. Generally, the coronal end of the broken instrument will lie against the outer or buccal surface of the root canal. Thus, the microtube 5 is inserted into the root canal with its longer side facing buccally and with the beveled end of the tube facing inwardly.

Figure 9:
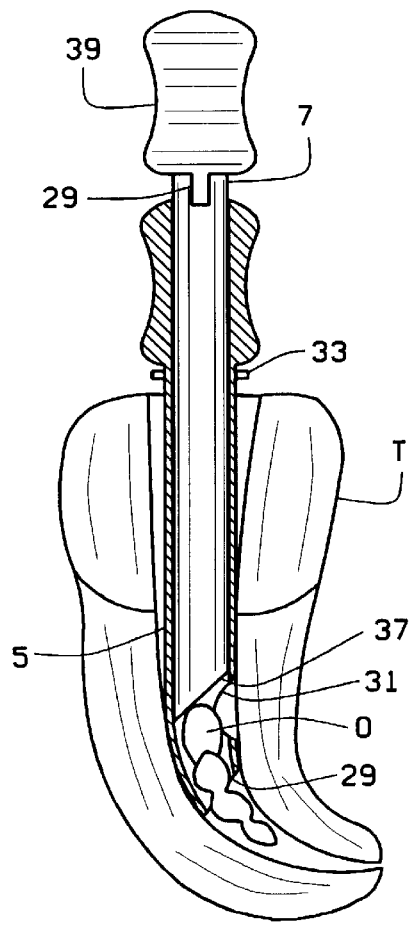
FIG. 9 is a cross-sectional view showing the application of the insert wedge to the obstruction within the microtube.
Figure 10:
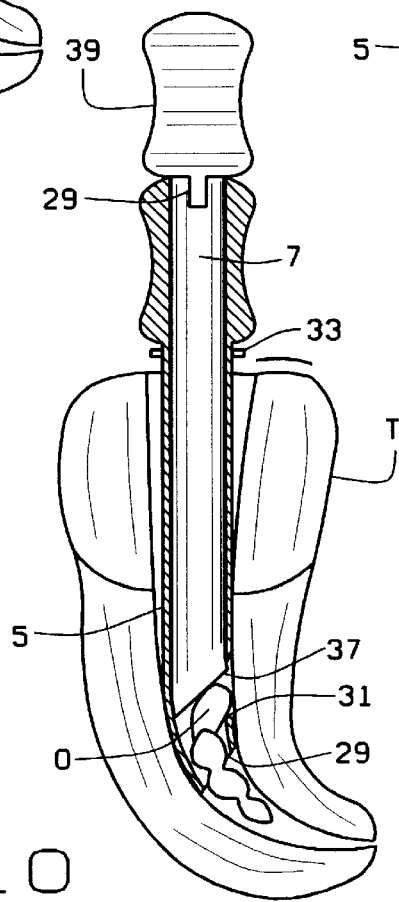
FIG. 10 is a cross-sectional view showing the use of the insert wedge and microtube to grasp the obstruction for removal of the obstruction from the root canal.

To engage the broken instrument O, the insert wedge or plunger 7 corresponding to the tube 5 of set 9 being used is selected. The insert wedge 7 preferably has a solid shaft 35 having a beveled distal end 37 and a handle 39 at the proximal end of the shaft 35. A pair of positioning guides 39 extend downwardly from the bottom side of the handle 39 and radially from the shaft 35. The wedge shaft 15 has a diameter sized to enable the wedge to be slidably inserted in the microtube 5. With the microtube 5 positioned in the root canal over the obstruction (broken instrument) so that the head of the obstruction is generally aligned with the microtube's cutout 31, the wedge 7 is inserted through the opened top end of the microtube and passed down its internal lumen until it contacts the broken obstruction, as shown in FIG. 9. The clinician lines up the insert wedge's orientation guides 39 with the microtube's slots 27. The positioning of the microtube's slots 27 and cutout 31 and the wedge's guides 39 assure that the beveled end 37 of the insert wedge will be positioned to push the coronal end of the obstruction through the cutout, as seen in FIGS. 9 and 10.

The broken obstruction is then engaged and secured by pushing the insert wedge 7 in an apical direction. The insert wedge's beveled end 37 will displace the head of the broken file O out through the microtube's cutout 31, as seen in FIG. 10. This action will create a strong purchase on the intracanal obstruction O. The broken instrument is retrieved by either counter rotating the assembled microtube 5 and insert wedge 7 together or by engaging the microtube's retentive hold 33 with an appropriate instrument and using a displacement force to pull the microtube 5 and insert wedge 7 (with the obstruction O) out of the root canal RC.

In view of the above, it will be seen that the several objects and advantages of the present invention have been achieved and other advantageous results have been obtained. As various changes could be made in the above constructions without departing from the scope of the invention, it is intended that all matter contained in the above description or shown in the accompanying drawings shall be interpreted as illustrative and not in a limiting sense. For example, although the microtube 5 and insert wedge 7 are separate, they could be packaged together, much the same way the body and plunger of a syringe are packaged together. Any other conventional means could be used to properly align the beveled end 37 of the insert wedge 7 in the microtube 5. For example, the bottom of the wedge handle could mate with the top of the microtube handle to align the beveled end of the wedge. Other rib and groove or channel configurations could also be used. Any of the trephine 3, tube 5, or plunger/wedge 7 can be adapted to induce vibrations in the obstruction to loosen the obstruction in the root canal. This can be done using piezoelectric energy or piezoelectric ultrasonic energy. This will facilitate withdrawal of the obstruction from the root canal. Although the handles of the trephine 3, the tube 5, and the plunger 7 are shown to be substantially the same size, the handle of the tube 5 can be smaller than the handles of the trephine 3 and the plunger 7. These examples are merely illustrative.

I claim:

1. A kit for removing an obstruction from a root canal of a tooth during an endodontic or retreatment procedure on a patient; the kit comprising a trephine sized to be inserted in the root canal and adapted to widen the root canal around the obstruction to expose the obstruction and an obstruction removal tool adapted to engage and grasp the obstruction to remove the obstruction from the root canal; the obstruction removal tool including:

a hollow tube defining a lumen and having a bottom end, a top end and a cutout spaced from the bottom end; the hollow tube having an outer diameter sized to be received in the root canal and an internal diameter sized to admit the obstruction into the lumen;

a plunger sized to be slidably received in the hollow tube from the top end of the tube; the plunger having a length sufficient to extend at least to the cutout in the hollow tube, the plunger having a bottom end and a top end; the bottom end of said plunger being beveled to urge a top end of the obstruction into the cutout; the plunger and tube cooperating to grasp the obstruction; and a guide which properly orients the bottom of the plunger in the hollow tube, such that said beveled end of said plunger faces said cutout of said hollow tube.

2. The kit of claim 1 wherein the trephine has a bottom end and a top end, the bottom end being hollow and having an inner diameter slightly larger then an upper end of the obstruction; the trephine including a cutting edge at its said bottom.

3. The kit of claim 2 wherein the cutting edge of said trephine comprises cutting flutes formed in the bottom of the trephine.

4. The kit of claim 1 wherein bottom end of said tube is beveled.

5. The kit of claim 1 wherein said guide includes a rib on one of said hollow tube and said plunger and a slot on the other of said hollow tube and plunger; said slot and rib being positioned on said hollow tube and plunger to position the beveled end of said plunger to face the cutout of the hollow tube.

6. The kit of claim 5 wherein the guide slot extends downwardly from the top of said hollow tube and the rib extends outwardly from an outer surface of the plunger.

7. The kit of claim 1 wherein the hollow tube includes retainers extending outwardly from an outer surface thereof.

8. A tool for removing an obstruction from a root canal of a tooth after the obstruction has been at least partially exposed; the tool including:

a hollow tube defining a lumen and having a bottom end, a top end and a cutout spaced from the bottom end; the hollow tube having an outer diameter sized to be received in the root canal, an internal diameter sized to admit the obstruction into the lumen, and a wall width at the bottom thereof sized to allow the bottom end of the hollow tube to pass over the top of the obstruction, such that at least the top of the obstruction is received in the lumen of the tube;

a plunger sized to be slidably received in the hollow tube from the top end of the tube; the plunger having a length sufficient to extend at least to the cutout in the hollow tube, the plunger having a bottom end and a top end; the bottom end of said plunger being beveled to urge a top end of the obstruction into the cutout; the plunger and tube cooperating to grasp the obstruction; and a guide which properly orients the bottom of the plunger in the hollow tube, such that said beveled end of said plunger faces said cutout of said hollow tube.

9. The tool of claim 8 wherein bottom end of said tube is beveled.

10. The tool of claim 8 wherein said guide includes a rib on one of said hollow tube and said plunger and a slot on the other of said hollow tube and plunger; said slot and rib being positioned on said hollow tube and plunger to position the beveled end of said plunger to face the cutout of the hollow tube.

11. The tool of claim 10 wherein the guide slot extends downwardly from the top of said hollow tube and the rib extends outwardly from an outer surface of the plunger.

12. The tool of claim 8 wherein the hollow tube includes retainers extending outwardly from an outer surface thereof.

13. A method for removing an obstruction from a root canal during an endodontic or retreatment procedure; the method including:

widening the root canal around a coronal end of the obstruction;

inserting a hollow tube into the root canal, the tube having a hollow end; said tube having an inner diameter at said hollow end sized to admit said obstruction to be received within said hollow end of said tube and an inner diameter; said tube being inserted into said root canal until at least a portion of said obstruction is received within said tube;

passing a plunger through said hollow tube to engage said obstruction; said plunger and hollow tube cooperating to mechanically grasp said obstruction; said plunger being passed through said hollow tube until said obstruction is mechanically grasped by said plunger and hollow tube; and removing the hollow tube and plunger from the root canal with the obstruction grasped thereby.

14. The method of claim 13 wherein said tube has cutout in a wall of said tube at said hollow end; said tube being inserted into said root canal until said top end of said obstruction is generally aligned with the cutout in the wall of said hollow tube.

15. The method of claim 14 wherein said plunger has a beveled bottom end adapted; said bottom end engaging said obstruction to urge said obstruction top end into said cutout; said plunger being slid axially through said hollow tube until said obstruction is urged through said cutout to mechanically grasp the top end of the obstruction.

* * * * *